(12) United States Patent
Katsen et al.

(10) Patent No.: US 6,539,664 B2
(45) Date of Patent: Apr. 1, 2003

(54) METHOD AND DEVICES FOR TREATMENT OF A BIOLOGICAL MATERIAL WITH A MAGNETIC FIELD

(75) Inventors: Alexander Katsen, Ramat Gan (IL); Tsur Dat, Sde Boker (IL); Yakov Yogev, D.N. Halutza (IL); Alexander Prilutsky, Beer Sheva (IL)

(73) Assignee: Pemsti Technologies Ltd., Arava (IL)

( * ) Notice: Subject to any disclaimer, the term of this patent is extended or adjusted under 35 U.S.C. 154(b) by 0 days.

(21) Appl. No.: 10/235,865

(22) Filed: Sep. 6, 2002

(65) Prior Publication Data

US 2003/0000132 A1 Jan. 2, 2003

Related U.S. Application Data

(63) Continuation of application No. 09/659,742, filed on Sep. 11, 2000, now abandoned, which is a continuation-in-part of application No. PCT/IL00/00428, filed on Jul. 19, 2000.

(30) Foreign Application Priority Data

Jul. 19, 1999 (IL) ................................................ 130982

(51) Int. Cl.$^7$ ................................................ A01G 7/04
(52) U.S. Cl. ........................................................ 47/1.3
(58) Field of Search ............................. 47/1.3, 58.1 R, 47/58.1 FV, 58.1 SE

(56) References Cited

U.S. PATENT DOCUMENTS 3,675,367 A   7/1972  Amburn
3,822,505 A   7/1974  Levengood (List continued on next page.)

FOREIGN PATENT DOCUMENTS

CH    CS 8100792 A  *  2/1986

(List continued on next page.)

OTHER PUBLICATIONS

Patent abstract of JP 9–275785, assigned to C I Kasei Co Ltd, published Oct. 28, 1997.

(List continued on next page.)

Primary Examiner—Peter M. Poon
Assistant Examiner—Jeffrey L. Gellner
(74) Attorney, Agent, or Firm—Browdy and Neimark, P.L.L.C.

(57) ABSTRACT

A device for the manipulation of a biological material by a magnetic field is presented. The device comprises a magnetic field source coupled to a current source. The current source is of a kind supplying an electric current of at least two electrical degree shifted phases. The magnetic field source comprises a two-part inductor, each inductor part producing a coordinate varying magnetic field (CVMF). Each inductor part is formed by at least two conductors aligned in a spaced-apart relationship, wherein each of the at least two conductors is connectable to a different phase of the current source, and has two spaced-apart parts arranged such that when the conductor is connected to the current source, the electric current flows in its two parts in opposite directions, respectively. The conductors of each inductor part are arranged such that each two locally adjacent conductor parts are associated with two different phases of the electric current source. A distance between the two conductor parts coupled to the same phase of the current source defines a half-wavelength $\lambda/2$ of a wave of magnetic induction of the CVMF. This distance is selected in accordance with a predetermined relation between the wavelength $\lambda$ and an effective space $\Delta$ within the magnetic field region defined by the dimensions of the biological material and its distance from the magnetic field source.

16 Claims, 7 Drawing Sheets

U.S. PATENT DOCUMENTS

| | | | |
|---|---|---|---|
| 4,251,950 A | | 2/1981 | Farque et al. |
| 4,266,532 A | | 5/1981 | Ryaby et al. |
| 4,587,957 A | | 5/1986 | Castel |
| 4,757,804 A | | 7/1988 | Griffith et al. |
| 5,077,934 A | | 1/1992 | Liboff et al. |
| 5,156,587 A | * | 10/1992 | Montone ............... 600/13 |
| 5,464,456 A | | 11/1995 | Kertz |
| 5,682,648 A | | 11/1997 | Miller |
| 5,740,627 A | | 4/1998 | Levengood et al. |
| 5,819,467 A | | 10/1998 | Zucker |
| 6,192,622 B1 | | 2/2001 | Haj-Yousef |
| 6,290,638 B1 | * | 9/2001 | Canedo et al. ............ 600/9 |

FOREIGN PATENT DOCUMENTS

| | | |
|---|---|---|
| CZ | 8100792 A | 2/1986 |
| DE | 2812546 A1 | 9/1979 |
| DE | 28 41 933 A1 | 4/1980 |
| DE | 36 13891 | 10/1987 |
| DE | 36 13 891 A1 | 10/1987 |
| DE | 91024161 | 5/1991 |
| DE | 91 02416.1 U1 | 6/1991 |
| DE | WO 93/15598 | 8/1993 |
| EP | 0 039 163 A1 | 11/1981 |
| EP | 0 392 626 | 10/1990 |
| EP | 0 459 540 A1 | 12/1991 |
| FR | 2704383 A1 | 11/1994 |
| GB | 2 145 317 A | 3/1985 |
| JP | 59-197262 A | 11/1984 |
| JP | 62 2602 40 | 11/1987 |
| JP | 3-19624 | 1/1991 |
| JP | 8/9810 | 1/1996 |
| JP | 8-56490 | 3/1996 |
| JP | 9-121682 | 5/1997 |
| JP | 9-187169 * | 7/1997 |
| JP | 2000-324910 | 11/2000 |
| RU | 2095966 | 11/1997 |
| WO | WO 84/00872 A1 | 3/1984 |
| WO | WO 99/35897 | 7/1999 |

OTHER PUBLICATIONS

Patent Abstract of JP 9–121682, assigned to Hitachi Metals Ltd., published May 13, 1997.

Derwent abstract of RU 20 95 966, by Tishchenko V V, published Nov. 20, 1997.

Patent abstract of JP 9–187169, assigned to Toda Kogyo Corp; Nishikawa Rubber Co Ltd; and Ooshita Sangyo KK, published Jul. 22, 1997.

Patent Abstracts of Japan: "JP 03 206820, Method for Cultivating Plant", applicant Yanmar Agricult Equip Co Ltd., published Sep. 10, 1991.

Kiyoshi Toko et al., "Growth and Electric Current Loops in Plants" Biophysical Chemistry, 33(1989) 161–176.

Derwent Patent Abstract, "SU 648 165 A, published Feb. 28, 1979, applicant Smirnov B V".

* cited by examiner

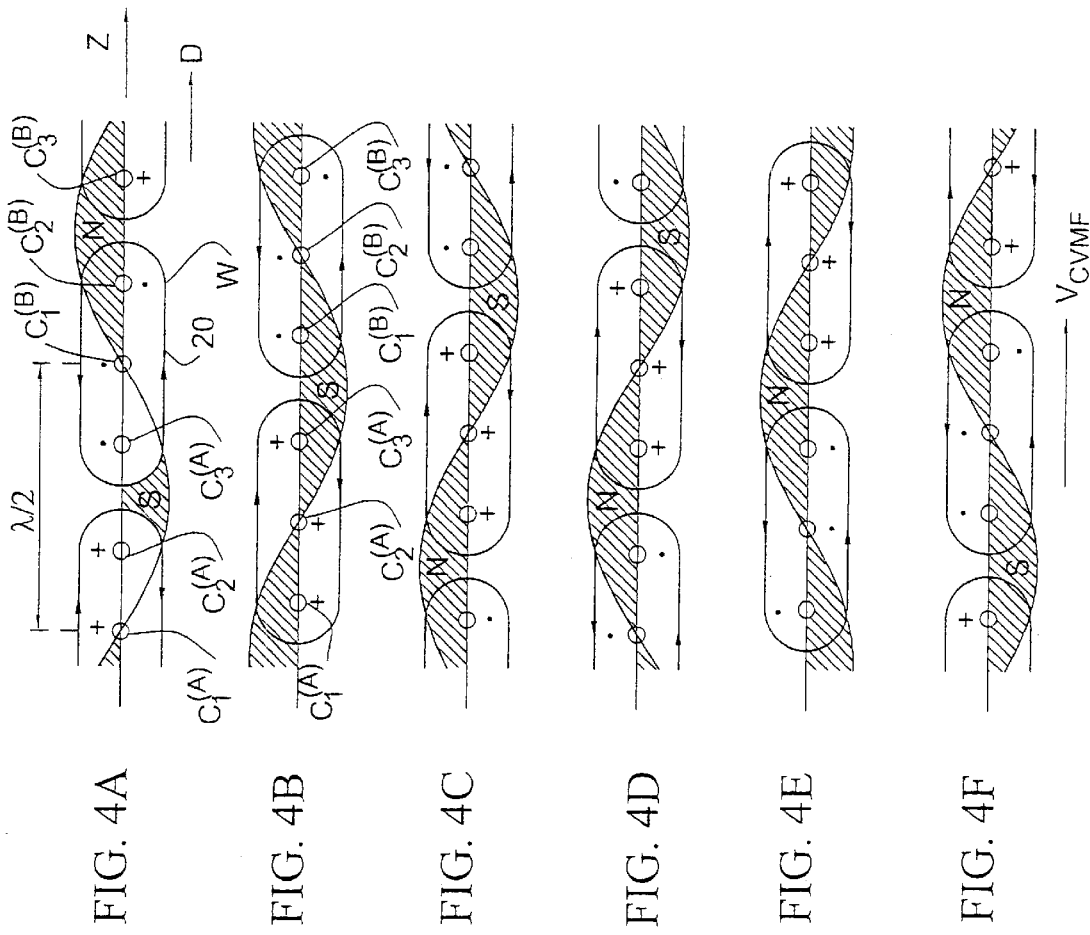
FIG. 4A
FIG. 4B
FIG. 4C
FIG. 4D
FIG. 4E
FIG. 4F
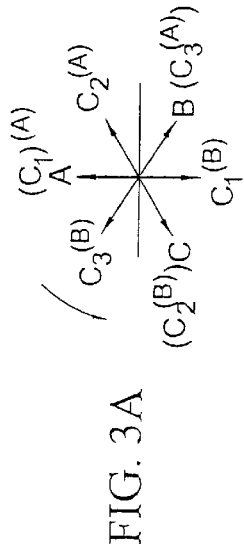
FIG. 3A
FIG. 3B
FIG. 3C
FIG. 3D
FIG. 3E
FIG. 3F

METHOD AND DEVICES FOR TREATMENT OF A BIOLOGICAL MATERIAL WITH A MAGNETIC FIELD

This is a continuing application of parent application Ser. No. 09/659,742, now abandoned, filed Sep. 11, 2000, itself a CIP of PCT/IL00/00428 filed Jul. 19, 2000, which designated the United States.

FIELD OF THE INVENTION

This invention relates to a method and devices for the treatment of a biological material with a magnetic field. The invention is useful in the treatment of plants and parts thereof, plant tissue culture, living cells, etc.

BACKGROUND OF THE INVENTION

Conventional vegetative plant propagation techniques for stimulating root formation in cuttings that are widely used in nurseries and greenhouses typically utilize various chemical materials for treating the cuttings and soil. This technique generally consists of the following. Cuttings that are to undergo the rooting process are taken from a tree. Foliage is removed only from the lower part of each cutting, while the upper part of the cutting remains foliaged. The foliage-free part of the cutting is then dipped into a powder or solution of a suitable hormone substance, such as the synthetic axin "Indolyl-3-Butric acid" (IBA), commercially available from Sigma Chemical CO., U.S.A. This chemical material penetrates through a relatively friable end section of the cutting, affecting the growth hormone thereof, and thereby stimulating the root formation. As to the upper, untreated part of the cutting, the foliage produces natural axin which is transferred towards the lower part and also affects the root formation at a further stage, the so-called "Mass Root Formation Treatment". More specifically, treated cuttings are transplanted into special trays filled with soil, where they are further treated over a long period of time on special tables provided with a heating system under the trays and a water sprinkling system.

Techniques of treating biological materials with a magnetic field have been developed, and are disclosed, for example, in the following publications: U.S. Pat. Nos. 4,587,957; 4,757,804; 5,077,934; EP 0459540; EP 0039163; EP 0392626; DE 3613891; RU 2095966; JP 62260240 and G 9102416.

According to some of these techniques, a biological material is subjected to a time-varying magnetic field, e.g., a pulsating magnetic field. However, such a field is typically created by solenoids or coils. The values of the magnetic induction of a magnetic field produced by a solenoid or coil change along one axis (that coincides with the geometrical axis of the solenoid or coil) and reach the amplitude value. Such a magnetic field is characterized by magnetic force lines that intersect the biological material under treatment, and are also oriented along the geometrical axis of the solenoid or coil. It is known that a biological material is characterized by its own microscopic and macroscopic currents occurring within the atoms, molecules, cells, tissues and organs. These currents, in turn, create magnetic fields. In accordance with the known law of electromagnetic induction, the pulsating field produced by a solenoid or coil creates an electromagnetic disturbance and a corresponding response inside the biological material, essentially in a plane perpendicular to the geometrical axis of the solenoid or coil. The disturbance and response vary with the changes in the values of the magnetic induction of the pulsating field.

The techniques directed towards altering the growth of a young tree utilize a strip formed by permanent magnets of alternating polarity mounted stationary around the stem of the tree, or the deposition of a mixture of a ferromagnetic powder on the stem and/or branches.

According to the technique disclosed in DE3613891 aimed at treating seeds, the magnetization of iron in the seeds by an external magnetic field is utilized.

SUMMARY OF THE INVENTION

The present invention provides for the manipulation of a biological material with a magnetic field by providing a novel method and device for subjecting a biological material in vitro or in vivo to a coordinate varying magnetic field, to produce a desired physiological effect.

The term "biological material" refers to material obtained from a biological source, having at least the complexity of a cell. This term refers both to eukaryotic and prokaryotic cells from either plant or animal source, present, for example, in a cell culture; to tissues (from plant or animal) present in a tissue culture, to isolated organs (such as plant stems, plant cuttings, bones, spine, heart, kidney, corneal blood bone marrow); to tissues present inside the organism, as well as to the full organism itself (both full plant and full animal organism).

The manipulation of the biological material may take place in vitro on isolated cells, tissues, or organs; may be carried out ex vivo on cells, or tissues which are manipulated and then returned to the body of the individual; or may be carried out in vivo.

The term "manipulation" in the context of the present invention refers to a change in at least one physiological property of said biological material. Typically, said manipulation is carried out in order to obtain a desired effect, as will be exemplified hereinbelow.

The term "desired effect" refers to the final physiological property the method is intended to achieve and may refer to such properties such as enhanced metabolism, enhanced circulation or diffusion, improved ion cell membrane permeability, increased growth, proliferation, viability, improved healing, propagation, as well as the enhanced flow of fluids. The results may also be the disintegration of aggregates and the targeting of pharmaceutical substances, as will be explained below.

The term "coordinate varying magnetic field" is a field that defines a magnetic field region (for a biological material to be located therein) and has a certain amplitude value of the wave of its magnetic induction, such that the amplitude value continuously displaces along the magnetic field region. The coordinate varying magnetic field (CVMF) is a field created by a system of magnetic poles that changes its position in time relative to the biological material located within the magnetic field region along at least one coordinate and in at least one direction. CVMF creates an electromagnetic disturbance and corresponding response inside the biological material in a plane inclined with respect to this at least one axis at a certain angle (e.g., right angle). This may, for example, lead to the creation of known magneto-hydro-dynamic effects. More specifically, if the biological material contains a liquid medium, CVMF can move the liquid medium inside the biological material in at least one direction along at least one coordinate. Another effect that can be achieved with the CVMF is the movement of a paramagnetic and ferromagnetic particle, as well as ions, in at least one direction along at least one coordinate. Additionally, the CVMF can cause the revolution of the particles. These effects are essentially different from those achieved with the pulsating fields that are characterized solely by time changes of their magnetic induction.

The term "subjecting" refers to the positioning of the biological material to be manipulated and a magnetic field source producing the CVMF with respect to each other, such that the biological material is located in or passes through the magnetic field region defined by the CVMF. This relative positioning should be such that an effective space Δ defined by the dimensions of the biological material and its distance from the magnetic field source is smaller than the half of a wavelength λ of the wave of the CVMF. The wavelength λ is defined by the accommodation of conductors of the magnetic field source.

By one aspect of the present invention, the manipulation of the biological material is achieved by directly subjecting the biological material to the magnetic field of the invention, without any need for the administration of any auxiliary substances.

It is known that all biological material contains electrolytes, which are effected to one degree or another by magnetic fields. Without wishing to be bound by theory, it is believed that by subjecting the biological material to a CVMF, at least one of the following physiological phenomena may take place:

1. The CVMF may enhance cytoplasmic flow inside cells. Said enhanced cytoplasmic flow inside cells may increase cellular metabolism, as well as improve the distribution of various nutrients, and intercellular factors within the cell. Said increase and said improvement may be utilized to improve proliferation, growth, viability, the propagation of differentiation of cells for cells present in an isolated cell culture, in tissues and tissue cultures, as well as in cells present in complex structures, such as organs kept in isolation, or inside the body.

For example, said improvement may be utilized to improve the growth of genetically engineered eukaryotic and prokaryotic cells grown in a bio-reactor, utilized for the production of desired biological material such as antibiotics, hormones, growth factors, and the like. It may improve growth rate, viability, and the proliferation of cells present in a tissue or in organs to be maintained for a prolonged period of time, or may increase the viability of the tissue or organ prior to implantation, for example, skin, cornea, kidneys, blood, bone marrow and the like. It may be used to improve the viability and proliferation of various organs and tissues present inside the body, for example to enhance healing processes of tissues such as cartilage, skin, bone, nerve muscle and the like.

Said enhancement may also be used to improve fertilization rate, if the magnetic field is applied to sperm, eggs or fertilized eggs kept in vitro, for example, for IVF purposes.

Where the method is used in connection with plants, it may be used to improve the rate of sprouting of plants from seeds, by increasing the viability and metabolism of each seed itself. In addition, it may be used to increase propagation from tissue culture, while at the same time decreasing the use of nutrients.

2. By another alternative, the CVMF may be used to improve or enhance the flow of electrolyte-containing liquids inside vessels such as blood or lymph vessels in animals, xylem or phlem vessels in plants, for example, to improve the transport of various beneficial substances, such as hormones, nutrients into vessels, or to enhance the clearance rate of various toxic substances through said vessels.

For example, the CVMF may be used in eukaryotic organisms to improve circulation, such as blood and lymph circulation through various blood and lymph vessels, especially in the periphery of the body. In the case of diabetes and other cases of obstructions of blood flow in small or large vessels, the coordinate-varying magnetic field may be used to improve said circulation. Another example is the improvement of blood flow to treat or alleviate impotence problems.

Another example is when the vessels are connected to various secretory glands, and application of coordinate-varying magnetic fields may be used to increase the secretion of various fluids from the glands and to improve their flow in the circulation. A specific example would be the mammary glands of lactating animals such as cows, sheep and goats, in which case the CVMF may be used to enhance and increase secretion of milk Another example is improvement of hormone secretion.

A specific example of the enhancement of flow, is the increase of flow in is plant xylem and phloem plantlets and plant cuttings which improve the provision of various nutrients to plant cells. The enhancement in connection with plants may also be the transport of various nutrients, the plant roots, or rootings.

3. By another alternative, a CVMF may be used to disintegrate various undesired aggregates present in biological material. The application of a CVMF to a biological material which contains electrolytes, which may also contain magnetic responsive material (such as for example iron present inside hemoglobin molecules) causes small vibrations at opposing directions of rotation and transportation, which may cause a disintegration of an aggregate.

By a specific example, where the aggregate is a blood clot, present inside a blood vessel, or an atherosclerotic clot present within a blood vessel, which partially, or completely blocks the blood vessel, the application of a CVMF may cause the integration of the aggregate into smaller particles which may be carried from the blocked site by the blood and cleared away.

Another aspect of the present invention is the manipulation of biological material by the objection to CVMFs, comprising also the administration of magnetic particles. The term "magnetic particles" refers to small units having magnetic properties, namely, those made of a ferromagnetic or paramagnetic material.

By one example, magnetic particles may be administered to the biological material, simply to enhance any of the above three physiological phenomena (enhancement of cytoplasmic flow, enhancement of flow inside vessels, and disintegration of particles) since the magnetic particles movement is effected by CVMF to a larger and more pronounced degree than the mere movement of electrolytes contained in biological liquids. However, by a preferred example, the lo magnetic particle may be (complexed, conjugated or coated) with a therapeutic agent, and the CVMF is used to target the complex (of magnetic particle-therapeutical agent) to a desired site in the biological material. Typically, this is a method carried out in vivo, wherein an individual is administered with said complexes, and then the CVMF is applied to the location where it is desired that the complex will concentrate, thus targeting the therapeutical material selectively to that region.

For example, the therapeutical agent may be an anti-cancer agent, such as cis platinum. The cis platinum is conjugated or complexed to magnetic particles, for example by coating magnetic particles with cis platinum.

The complexes are then administered to a subject having a localized cancer growth, for example, in a specific lymphnode, breast cancer, colon cancer, etc., and the CVMF is applied to the location of the tumor growth. Then, the conjugates of the magnetic particles/therapeutical substance which are present in the blood are directed by the CVMF towards a tumor growth site (due to the movement of the magnetic poles system created by the CVMF), so that their concentration at the desired site (being the tumor growth site) is much larger than the general concentration in the body, thus destroying the tumor in a selective manner.

There is thus provided according to one aspect of the present invention, a device for the manipulation of a biological material by a magnetic field, comprising a magnetic field source coupled to a current source for producing said magnetic field, the device being characterized in that:

the current source is of a kind supplying an electric current of at least two electrical degree shifted phases;

the magnetic field source comprises a two-part inductor, each inductor part producing a coordinate varying magnetic field (CVMF), wherein each inductor part is formed by at least two conductors aligned in a spaced-apart relationship, each of the at least two conductors being connectable to a different phase of the current source, each of the at least two conductors having two spaced-apart parts arranged such that when the conductor is connected to the current source, the electric current will flow in its two parts in opposite directions, respectively, the conductors being arranged such that each two locally adjacent conductor parts are associated with two different phases of the electric current source;

a distance between the two conductor parts coupled to the same phase of the current source defines a half-wavelength $\lambda/2$ of a wave of magnetic induction of said CVMF, and is selected in accordance with a predetermined relation between the wavelength $\lambda$ and an effective space $\Delta$ within the magnetic field region defined by the dimensions of the biological material and its distance from the magnetic field source.

According to another aspect of the present invention, there is provided a method for the manipulation of a biological material to change at least one physiological property of the biological material to obtain a desired effect, the method comprising the steps of creating a magnetic field defining a magnetic field region for the biological material to be located therein, the method being characterized in:

(a) creating said magnetic field by creating a system of magnetic poles that changes its position in time along at least one coordinate and in at least one direction, said magnetic field being thereby a coordinate varying magnetic field (CVMF) that defines said magnetic field region and has an amplitude value of a wave of its magnetic induction continuously displaced along the magnetic field region in said at least one direction along said at least one coordinate, the magnitude of the magnetic induction being sufficient to cause said change of the at least one physiological property of the biological material;

(b) selecting the wavelength $\lambda$ of the wave of the magnetic induction and an effective space $\alpha$ within the magnetic field region, defined by the dimensions of the biological material and its location relative to the magnetic field source, in accordance with a predetermined condition of a relation between them; and (c) locating the biological material within the magnetic field region for a time period sufficient for causing said change to obtain said desired effect.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A–3F and 4A–4F illustrate the main operational principles of the device of FIG. 1;

DETAILED DESCRIPTION OF THE INVENTION

Figure 1:
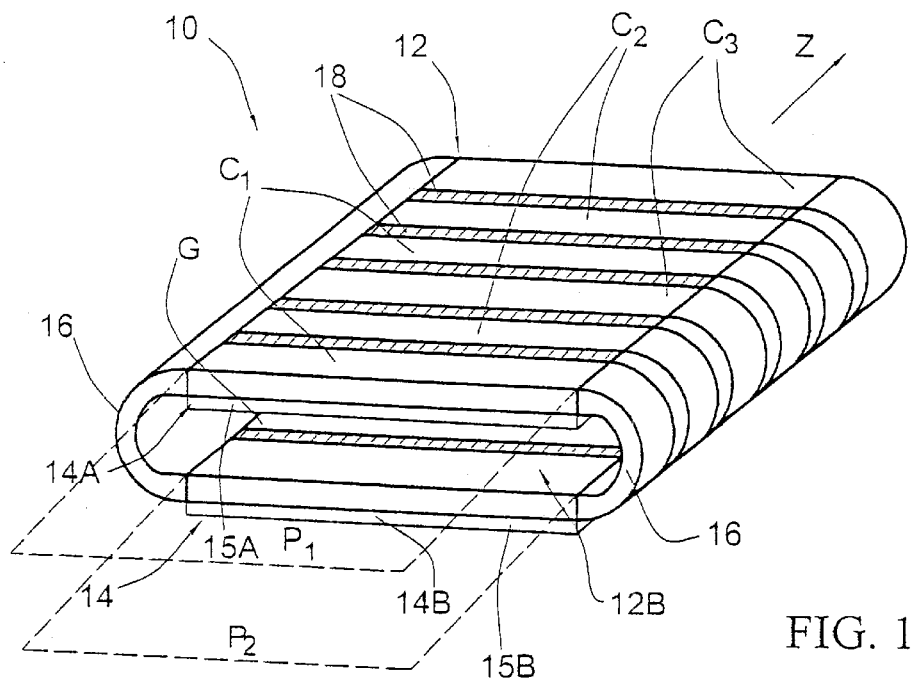
FIG. 1 is a schematic illustration of a device according to the invention.
Figure 2:
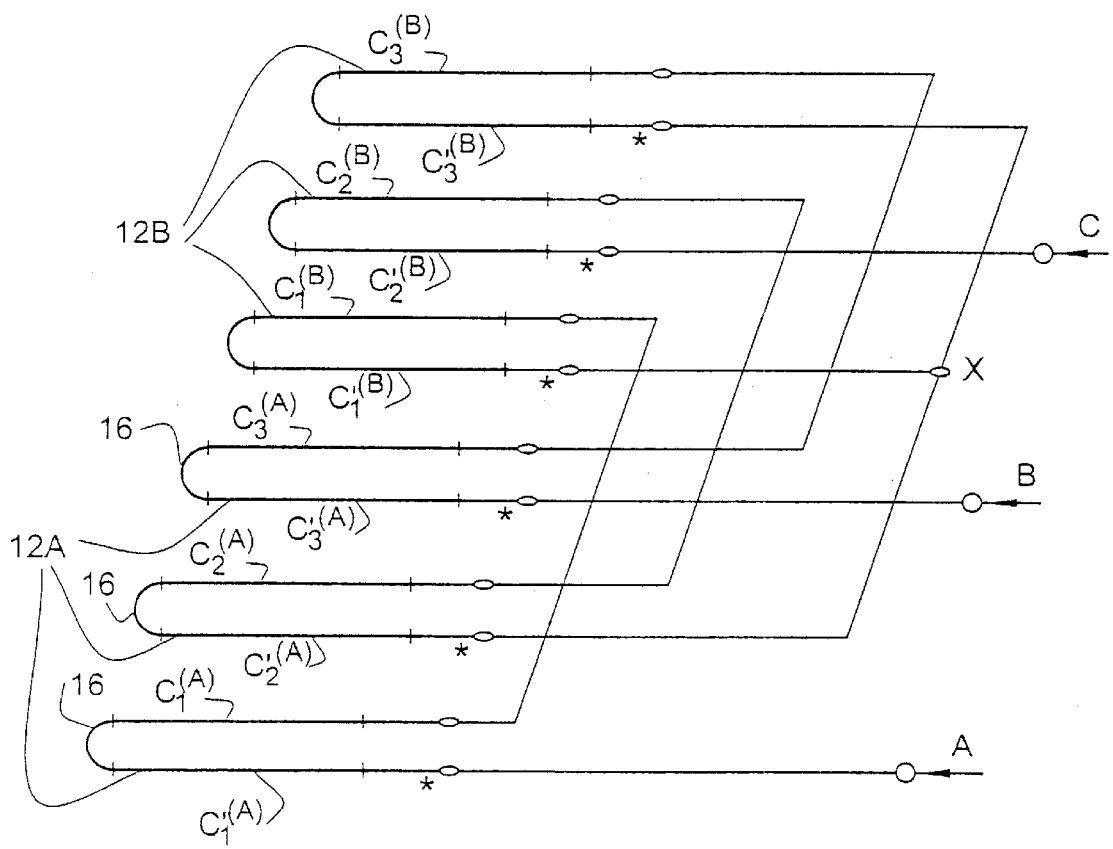
FIG. 2 more specifically illustrates the electrical connection between conductors in the device of FIG. 1.

Referring to FIGS. 1 and 2, there is illustrated a device 10 according to the invention presenting a magnetic field source capable of producing a coordinate varying magnetic field (CVMF) defining a magnetic field region for a biological material to be located therein. This region will be called below as a "treatment zone". The device 10 comprises a two-part inductor 12. In this specific example, two inductor parts 12a and 12b are located in two parallel spaced-apart planes $P_1$ and $P_2$ defining a gap G therebetween. Each inductor part is formed of a plurality of spaced-apart conductors—three conductors $C_1$–$C_3$ (and $C_1'$–$C_3'$) in the present example, mounted on a magnetic circuit 14. The conductors are coupled to a three-phase current source, which is not specifically shown. In this specific example, the device 10 is designed so as to produce a three-phase CVWF, as will be described more specifically further below.

The arrays 12a and 12b are physically connected through so-called "frontal idle" parts 16 of the conductors which are not involved in the creation of a magnetic field and are located outside the treatment zone. The treatment zone may be located within the gap G between the arrays 12a and 12b, or/and at either one of the opposite sides of the inductor, or/and at opposite sides of the inductor. Generally speaking, when a magnetic circuit is used, the treatment zone may be a two-part zone (one part located in the gap, and the other in the vicinity of either one of the outer surfaces of the inductor), and may be a three-part zone, when no magnetic circuit is used.

The conductors $C_1$–$C_3$ and $C_1'$–$C_3'$ are arranged so as to form two parallel spaced-apart arrays forming, respectively, the inductor parts 12a and 12b. As better seen in FIG. 2, each conductor has two parts ("halves"), which are spaced from each other, and is coupled to a different phase of the current source, as compared to other conductors. An electric current flows in the two parts of each conductor in the opposite directions, respectively.

More specifically, conductor $C_1$ has two spaced-apart parts $C_1^{(A)}$ and $C_1^{(B)}$; conductor $C_2$ has two parts $C_2^{(A)}$ and $C_2^{(B)}$; and conductor $C_3$ has two parts $C_3^{(A)}$ and $C_3^{(B)}$. Similarly, in the array 12b, conductor $C_1'$ has two spaced-apart parts $C'_1{}^{(A)}$ and $C'_1{}^{(B)}$ with opposite directions of the electric current flows therein; conductor $C_2'$ has two parts $C'_2{}^{(A)}$ and $C'_2{}^{(B)}$; and conductor $C_3'$ has two parts $C'_3{}^{(A)}$ and $C'_3{}^{(B)}$. The conductors of each inductor part are arranged such that each two locally adjacent conductor parts are coupled to different phases of the current source. Two parts $C_1^{(A)}$ and $C_1^{(B)}$ of conductor $C_1$ are coupled to a connection port A (through a common point X) leading to one of the three phases of the power network; two parts $C_2^{(A)}$ and $C_2^{(B)}$ of conductor $C_2$ are connected to a connection port C (leading to the second phase); and the two parts $C_3^{(A)}$ and $C_3^{(B)}$ of conductor $C_3$ are connected to a connection port B (leading to the third phase of the three-phase power network).

In this specific example of FIG. 2, the conductors of two arrays (i.e., two inductor parts) 12a and 12b are also electrically connected so as to be coupled to a common three-phase current source. This is implemented by electrically connecting the two parts of each conductor of one inductor part to each other through a corresponding conductor (i.e., its two conductor parts) of the other inductor part. For example, with respect to conductor $C_1$, its two parts $C_1^{(A)}$ and $C_1^{(B)}$ are electrically connected to each other via the conductor parts $C'_1{}^{(A)}$ and $C'_1{}^{(B)}$. It should, however, be understood that the inductor parts could be separately supplied from respective current sources.

It should be noted that the inductor can be designed so as to be connected to a two-phase current source. To this end, each inductor part may comprise two conductors each connected to a corresponding one of two phases of a two-phase current source. Alternatively, the above-described inductor 12, in which each inductor part is formed by three conductors, can be coupled to a two-phase current source. In this case, the two ports (e.g., B and C) would be connected to a common phase through a capacitor.

In the case of the three-phase power network, a three-phase electric circuit is provided in each of the inductor parts 12a and 12b, such that the electric currents passing through the locally adjacent conductor parts in the array have three different phases A, C and B which are displaced by 120 electrical degrees. In the case of a two-phase power network, a 90 electrical degree shift between the locally adjacent conductor parts (of each array) will be provided.

Turning back to FIG. 1, in this specific example, the conductors are mounted on the magnetic circuit 14 of the so-called "slots-and-teeth" kind having two parts 14a and 14b associated with inductor parts 12a and 12b, respectively. Teeth 18 extend along base (support) plates 19a and 19b in a spaced-apart parallel relationship defining slots (not shown) therebetween for the conductors $C_1$–$C_3$ (and $C_1'$–$C_3'$) to be mounted in the slots. The teeth 18 serve as concentrators of the magnetic field, thereby creating a high-gradient magnetic field. The concentrators 18 may be made from a ferromagnetic shot or from thin sheets of the electrical transformer steel.

It should be noted that here the support plates 19 of the magnetic circuit parts 14a and 14b, respectively, are shown as extending along, respectively, the inner surface defined by the inductor part 12a, and the outer surface defined by the inductor part 12b. This is particularly suitable for the case when the treatment zone is a two-part zone, one part being located above the inductor part 12a, and the other part being located within the gap G. Other implementations are also possible, as will be described further below with reference to FIGS. 6 and 8. To this end, the magnetic circuit 14 is constructed such that the support plates 19a and 19b are removable, in order to adjust their location in accordance with the location of the treatment zone to meet the requirements of a specific application.

Thus, in the example of FIGS. 1 and 2, the three-phase electric circuit is provided in each of the inductor parts 12a and 12b, the electric currents passing through these conductors having three different phases A, B and C displaced by 120 electrical degrees.

FIGS. 3A–3F illustrate a rotary current vector diagram of the conventional commercial power network (for example, 50–60 Hz), showing, respectively, the situations at six successive moments of time. FIGS. 4A–4F illustrate corresponding changes in the current directions in the conductor parts of the conductor array (one inductor-part, e.g. 12b). Here, the opposite directions of electric current (towards and away from the observer) are shown as "•" and "+", respectively.

The above-described arrangement of conductors of each inductor creates a system of magnetic poles formed by the magnetic force lines 20 of the magnetic field produced by the passage of currents of shifted phases through the adjacent conductors. Due to the phase rotation, this system of poles changes its position in time along a Z-axis, in a direction D. The time changes in the location (coordinate along the Z-axis) of the magnetic poles N and S are shown in the FIGS. 4A–4F in a self-explanatory manner. Hence, the magnetic field produced by this inductor is a coordinate varying magnetic field (CVMF).

The variation of values of the magnetic induction of this field presents a wave W. The space of propagation of the wave W along the Z-axis defines a magnetic field region extending along this axis. The amplitude value $B_{amp}$ of the magnetic induction continuously displaces along the magnetic field region. A biological material, whilst being located in this region (treatment zone) becomes subjected to the CVMF.

It is thus evident that the magnetic field created by each inductor part is coordinate varying, namely, is such that the coordinate of the system of poles changes in time. This is achieved due to the rotation of the electric current phase that produces the effect of the poles' movement with the velocity V along the Z-axis, the orientation of which with respect to the device 10 is shown in FIG. 1. Thus, the device 10 formed by such linear multi-pole conductors creates a CVMF in a manner to cause a movement of waves (system of poles) along the Z-axis. It should be noted that by appropriately supplying the inductor, the direction of movement of the system of poles could be changed to the opposite one. For some applications, this change of the direction of movement can be performed periodically.

It should be understood that CVMF is a "varying" (changing) field, namely, the field produced by time changes in the coordinate (position) of the system of poles and changes in the magnitude of magnetic induction along the Z-axis. The propagation of the wave of electric and magnetic fields (e.g., a light wave) is analogous to the wave running along a string. The CVMF does not mean that a part of the string moves along the direction of wave propagation, but rather means that the displacement of the string sequentially appears in successive parts of the string. This effect is essentially different from the effect of periodical appearance of the amplitude value of a magnetic field wave at a certain location on the geometrical axis of a solenoid or coil, as obtained with the conventional time-varying magnetic field produced thereby.

The CVMF has a half-wave ($\lambda/2$), the length of which is defined by a distance between the conductors in the array characterized by the same phase and opposite directions of electric currents, namely between conductors $C_1^{(A)}$ and $C_1^{(B)}$, $C_2^{(A)}$ and $C_2^{(B)}$, $C_3^{(A)}$ and $C_3^{(B)}$. The half-wave $\lambda/2$ is also determined as the distance between two locally adjacent opposite-polarity amplitude values of the magnetic induction. The velocity V of the displacement of the amplitude values (wave) of magnetic induction of the CVMF is determined in accordance with the following relationship:

$$V = \lambda \cdot f$$

wherein $\lambda$ is the wavelength of the CVMF; f is the frequency of the alternating electric current, for example of the commercial power network.

As indicated above, the electric current passes in two opposite directions in the two parts, respectively, of each conductor. As for the electric current flow in two opposite conductor parts ($C_1^{(A)}$ and $C'_1^{(A)}$, $C_2^{(A)}$ and $C'_2^{(A)}$, etc.) of two opposite inductor parts 12a and 12b, respectively, the following should be noted. By appropriately supplying the inductor parts 12a and 12b, and appropriately accommodating a magnetic circuit, if any, either the opposite directions of electric current in two opposite conductors is provided thereby creating magnetic force lines forming N-N (or S-S) orientation of poles, or the same direction of the electric current in two opposite conductors is provided thereby creating magnetic force lines forming N-S orientation of poles. The N-N (or S-S) orientation of poles is formed by the longitudinal closing of the magnetic force lines (i.e., along the gap between the inductor parts 12a and 12b), while N-S orientation of poles is formed by the transverse closing of the magnetic force lines (across the gap). To provide the N-N (or S-S) orientation of poles in the treatment zone located in the gap between the two inductor parts, the plates 19a and 19b of the magnetic circuit should be located at outers surfaces of the inductor parts. This will be described below with reference to FIG. 6.

The above example of FIGS. 4A–4F illustrates the case of a bi-polar CVMF (i.e., N-S-N-S- . . . ) produced by the inductor part. In this case, the distance between each two locally adjacent amplitude values of the magnetic induction is determined as the distance between two locally adjacent opposite magnetic poles, and is actually the half-wavelength $\lambda/2$. Such a bi-polar CVMF is achieved by supplying a two-half-period alternating current to the conductors of each phase. Currents induced by such a bi-polar CVMF in a biological material located in the magnetic field region will change their directions along with the changes of the polarity of the wave of the magnetic induction.

It should, however, be noted, although not specifically shown, that the CVMF produced by either inductor part may be of an uni-polar type. (N-N-N- . . . or S-S-S- . . . ). This may be achieved by using a diode, namely, supplying a one-half-period alternating current to the conductors of each phases. In this case, the distance between two locally adjacent amplitude values of the magnetic induction is determined as the distance between two locally adjacent identical magnetic poles, and is actually the wavelength $\lambda$. Currents induced in the biological material by such a unipolar CVMF will flow in one direction only.

Figure 5:
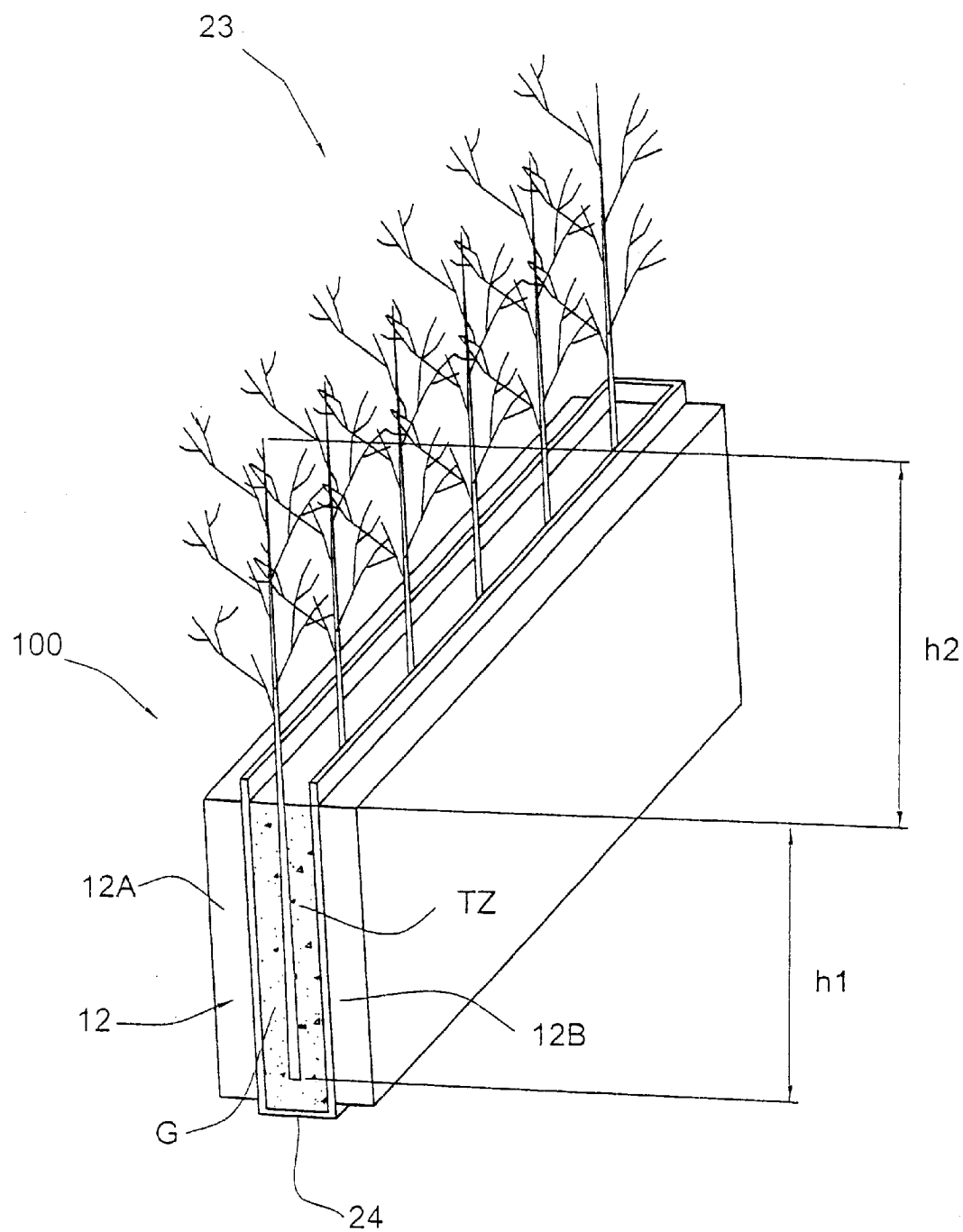
FIG. 5 illustrates a device according to the invention being used for the simultaneous treatment of a group of cuttings to stimulate the rooting process.

FIG. 5 illustrates a device 100 according to the invention used for the simultaneous treatment of a group of cuttings, generally at 23, aimed at stimulating the root formation process. The device is comprised generally similar to the above-described device 10, namely, comprises the two-part inductor 12, the two parts (conductor arrays) 12a and 12b being located in two parallel spaced-apart planes, respectively. For the purposes of this specific application, a treatment zone TZ is located in the gap between the two inductor-parts 12a and 12b. The device 100 also comprises an elongated vessel 24 of a substantially rectangular shape (the so-called "slot-like vessel") located in the treatment zone.

The lower, foliage-free stem portions of the cuttings 23 having the length $h_1$ are inserted into the slot-like vessel 24, being thereby enclosed between the two parts 12a and 12b of the inductor, so as to be within the magnetic field region produced by the magnetic field source 100. The foliaged stem portions having the length $h_2$ are located outside the vessel 24 and outside the magnetic field region. Hence, the foliage-free stem portion (constituting a root formation zone) is treated by the CVMF.

It should be noted that the provision of the vessel 24 is optional, as such a slot-like space for installing the cuttings therein may be defined as the space between the inductor parts 12a and 12b. Hence, the vessel 24 constitutes the slot-like space within the magnetic field region produced by the magnetic field source 100. The vessel (space) 24 may or may not be filled with water or a hormone substance, which is therefore not specifically shown.

In order to facilitate the understanding of the effect of the device 100 with respect to the rooting process, it would be reasonable to consider the construction of a stem and natural processes occurring therein. As known, the pre-root cells, callus, is typically formed in a cambium cells layer. The formation of callus can be activated by the transport of liquid phase towards the cambium cells layer through the apoplast pathway, which depends on the firmness of cortex. In other words, the "substance-transport" parameter of a stem altering the growth behavior of the cutting is defined by the liquid permeability through the stem in a radial direction, i.e., from the stem's surface to the cambium cells layer.

It was found that radial and longitudinal electric current (ions) loops take place inside a cutting stem ("*Growth and Electric Current Loops in Plants*", Biophysical Chemistry 33 (1989), 161–176). The interaction between the CVMF and these radial electric current loops creates mechanical force effects, namely tensile and compressive stress in the epidermis and endodermis tissues. The magnetic force lines of the CVMF are directed substantially perpendicular to the surface region of the cutting stem, namely perpendicular to the radial electric current (ions) loops inside the stem causing a so-called "pushing" of these loops. This is actually an "electromagnetic stress" that, similar to vibrations, "massages" the cambium cells layer, thereby stimulating the callus formation. Such vibrations increase the friability of the stem cortex, thereby increasing the permeability of liquid therethrough in the radial direction, and decreasing the time for root initiation. If such a liquid contains a hormonal substance, the quantity of the substance reaching the cambium is increased, yet further accelerating the further root-development process. On the other hand, the CVMF itself influences on the activity of the cambium cells layer.

Figure 6:
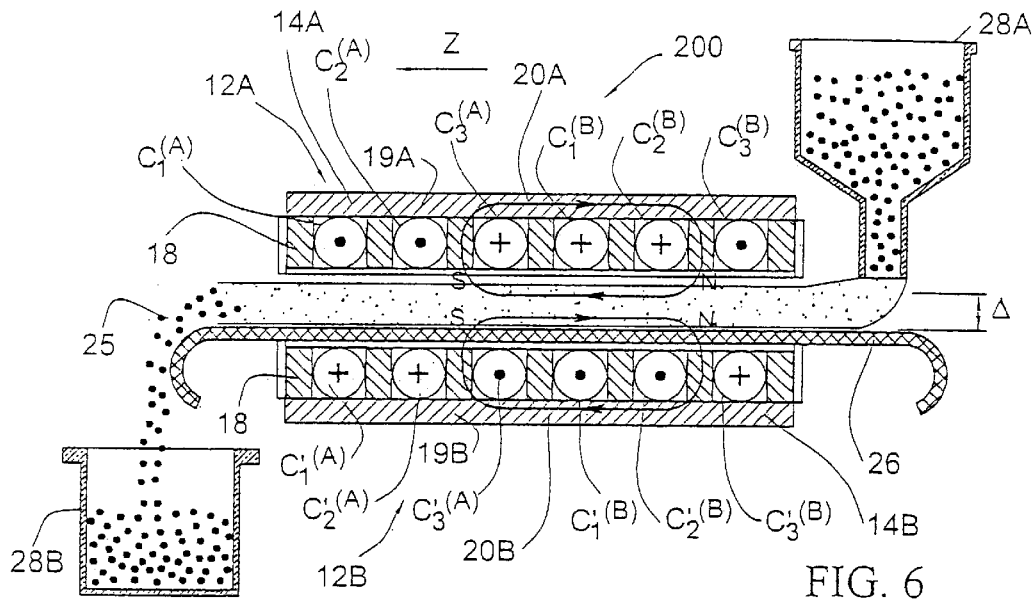
FIG. 6 illustrates a device according to the invention being used for the treatment of seeds.

FIG. 6 illustrates a device 200 according to the invention used for the treatment of seeds, generally at 25. The device is generally similar to the previously described examples, the treatment zone being located within the gap between the inductor-parts 12a and 12b. The support plates 19a and 19b of the magnetic circuit extend along the outer surfaces of the inductor parts 12a and 12b, respectively. A conveyor belt 26 is provided, accommodated so as to convey the seeds along the Z-axis through the treatment zone. The seeds are supplied onto the conveyor from a feeding vessel 28A and discharged from the conveyor into a collecting vessel 28B. The treatment zone occupied by the seeds 25, i.e., an effective space within the gap between the inductor-parts 12a and 12b to be treated by the magnetic field produced by the inductor, has a certain height $\Delta$, the so-called "working gap".

As clearly illustrated in the figure, the electric currents in the opposite conductors ($C_1^{(A)}$–$C'_1^{(A)}$, $C_2^{(A)}$–$C'_2^{(A)}$, etc.) of the inductor parts 12a and 12b flow in opposite directions (i.e., "+" and "•"), thereby providing the opposite directions of magnetic force lines 20a and 20b, respectively, with the longitudinal closing thereof (along the gap), thus forming the N-N (and S-S) orientation of poles within the treatment zone (the magnetic field region).

As indicated above, although not specifically shown, the electric currents in the opposite conductors ($C_1^{(A)}$–$C'_1^{(A)}$, etc.) may be of the same direction (e.g. "+" and "+", or "•" and "•"), forming thereby the N-S orientation of poles, the magnetic force lines closing across the gap.

Due to the phase difference between the electric current passing through the locally adjacent conductor parts, the magnetic poles "moves" along the Z-axis. The velocity of the poles' movement is determined as described above.

The provision of the conveyor 26 is associated with the fact that CVMF is non-uniform along the inductor part. This is due to the accommodation of the conductor parts of each inductor-part in a spaced-apart relationship along the length of the inductor part, and partly due to the slots-and-teeth design of the magnetic circuit. Therefore, the seeds have to be moved along the inductor, thereby creating the same conditions not only in the longitudinal direction, but also in the transverse direction within the working gap $\Delta$.

In order to achieve effective treatment of all the seeds in the working gap $\Delta$ with the CVMF produced by the inductor, a relation between the wavelength $\lambda$ of the CVMF and the working gap $\Delta$ should satisfy a certain condition.

In the case of two-part inductor with the longitudinal closing of the magnetic force lines (i.e., along the gap), this condition is as follows: $\lambda/2 > \Delta/2$. In the case of two-part inductor with the transverse closing of the magnetic force lines (i.e., across the gap), this condition is as follows: $\lambda/2 > \Delta$.

Figure 7:
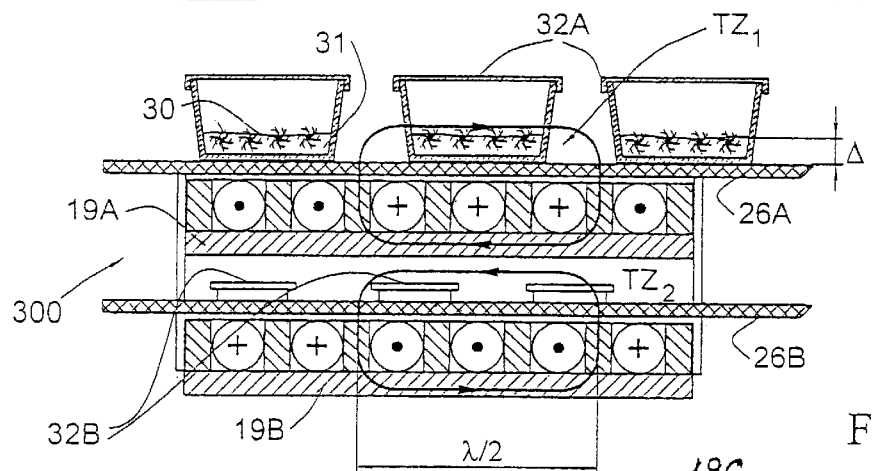
FIG. 7 illustrates a device according to the invention being used for the treatment of plant tissue culture.

FIG. 7 illustrates a device 300 according to the invention being used for the treatment of a plant tissue culture, generally at 30. The latter is immersed in layers of nutrient substance (agar) 31 having a certain thickness $\Delta$ located in substantially identical vessels 32a and 32b. The thickness $\Delta$ of the agar layer 31 is such as to be sufficient for nourishing the tissue culture during a preset time period.

The device 300 is constructed generally similar to the previously described examples, namely comprising the two-part inductor. The vessels 32a and 32b are mounted on the belt conveyors 26a and 26b driven for movement along the inductor. Here, however, the treatment zone is a two-part zone, one part $TZ_1$ being located above the upper inductor part 12a, and the other part $TZ_2$ being located inside the gap between the inductor parts 12a and 12b. The conveyors 26a and 26 are thus mounted for movement along the zones $TZ_1$ and $TZ_2$, respectively. In this specific example of two-part treatment zone, the magnetic circuit is constructed such that one support plate 19a extends along an inner surface defined by the upper inductor part 12a, while the other plate 19b extends along an outer surface defined by the lower inductor part 12b. It should be understood that although in this example the electric current in each two opposite conductors flows in opposite directions (and consequently, the magnetic force lines close along the gap), but the two inductor parts actually operate as two separate one-side inductors with respect to two separate treatment zones, respectively, the condition $\lambda/2 > \Delta$ should be satisfied.

Figure 8:
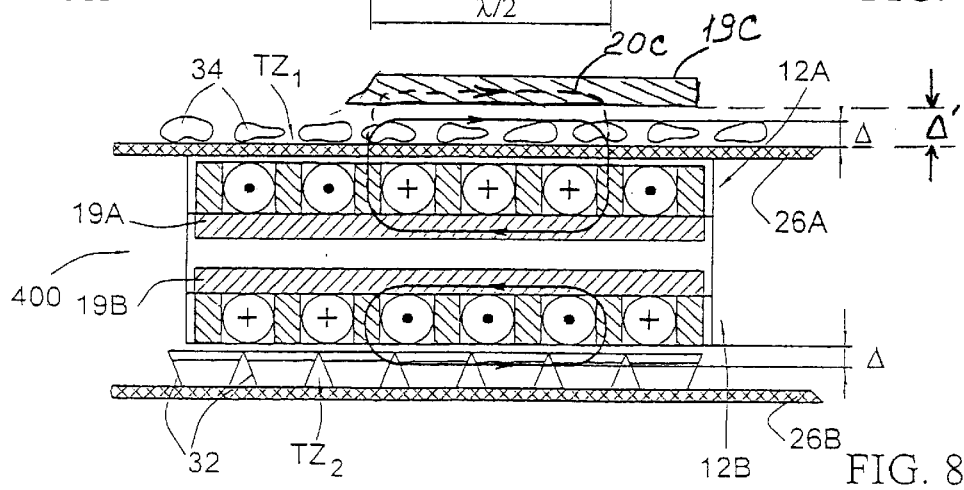
FIG. 8 illustrates a device according to the invention being used for the simultaneous treatment of seeds in soil and vegetable organisms.

FIG. 8 illustrates a device 400 according to the invention used for the simultaneous treatment of potato tubers, generally at 34 (of a kind for further transplantation into soil), and of seed planting in soil (not shown here) located inside the trays 32, in two treatment zone parts $TZ_1$ and $TZ_2$, respectively. The treatment zone parts $TZ_1$ and $TZ_2$ are located at opposite sides of the inductor, respectively, namely, above the outer surface defined by the upper inductor part 12a, and below the outer surface defined by the lower inductor part 12b. Accordingly, the support plates 19a and 19b are accommodated so as to extend along the inner surfaces defined by the inductor parts 12a and 12b, respectively. The potato tubers 34 and the plant tissue culture containing vessels are mounted on the conveyors 26a and 26b, respectively, that convey them through the treatment zone parts $TZ_1$ and $TZ_2$. The dimensions of the potato tubers 34 on the conveyor 26a, as well as the distance between the inductor part 12b and the planting depth of seeds in soil, define the working gap $\Delta$. For both inductor parts, the relationship $\lambda/2 > \Delta$ should be satisfied.

As shown, an additional magnetic circuit 19c (similar to support plates of the magnetic circuits 19a and 19b, e.g., made of transformer steel) can be accommodated above the conveyor 26a, i.e., above the treatment zone $TZ_1$. This additional magnetic circuit 19c results in magnetic force lines 20c (shown in dashed lines) closing along the treatment zone $TZ_1$ that provide even more concentration of the magnetic field in the treatment zone. In other words, the use of the additional magnetic circuit significantly improves the electromagnetic parameters of the device: less energy is required for creation of the same magnetic field as that produced without the additional magnetic circuit. In this case, a working gap $\Delta'$ is determined as the distance between the surface of the plate 19c facing the treatment zone and the conveyor belt 26a supporting the potato tubers 34.

Figure 9A:
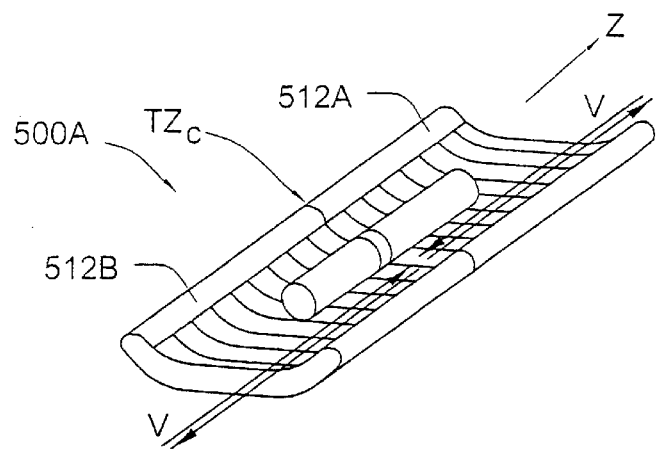
FIGS. 9A and 9B illustrate two different examples, respectively, of the implementation of a device according to the invention suitable for in vivo treatment of a biological material.
Figure 9B:
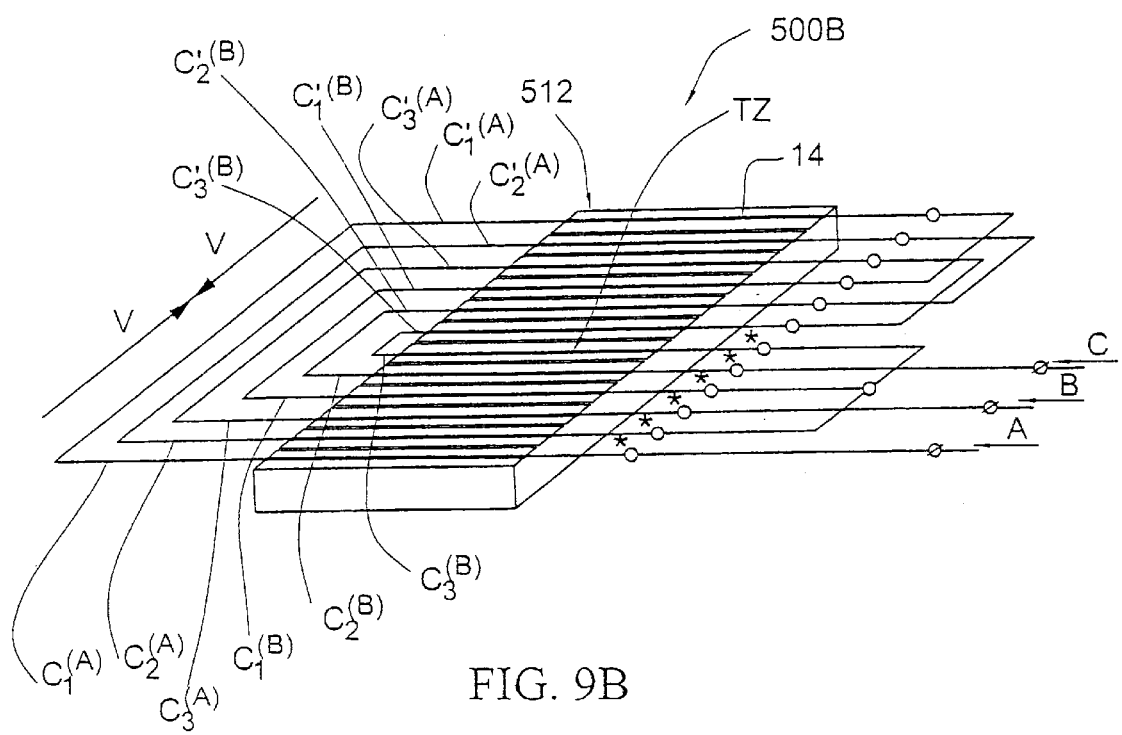

Referring now to FIGS. 9A and 9B, there are illustrated two examples of the implementation of a device according to the invention suitable for in vivo treatment of a biological material, such as the patient's bone. In both examples, the device is constructed such as to produce a CVMF directed towards and away of the center of a treatment zone $TZ_c$ (the location in the bone to be treated).

In the example of FIG. 9A, the device 500a comprises two symmetrically identical inductors 512a and 512b, each being constructed similar to the previously described examples, which is therefore not specifically shown. The symmetrical identity of the inductors 512a and 512b signifies that the conductors of these inductors are arranged symmetrically identical and connected to a two- or three-phase power network, so as to produce the CVMFs in +Z and −Z directions. The treatment zone extends from the ends of the inductors 512a and 512b towards a boundary region between the inductors 512a and 512b (the center of the treatment zone $TZ_c$ being located in the vicinity of the boundary region). The waves of the CVMFs produced by the inductors 512a and 512b move towards or away form each other with the same velocity V. The periodical change of the direction of movement of the waves to the opposite one results in the change of the direction in which the CVMF influences on a biological material located in the center of the treatment zone, and promotes the better metabolism of the vital activity of tissue.

In the example of FIG. 9B, the device 500b comprises a single inductor 512, which has a somewhat different construction, as compared to the previously described examples. Here, all the conductors parts $C_1^{(A)}$, $C'_1^{(A)}$, $C_1^{(B)}$, $C'_1^{(B)}$, $C_2^{(A)}$, $C'_2^{(A)}$, $C_2^{(B)}$, $C'_2^{(B)}$, etc. are located in a common plane P, but similar to the above examples, the two parts of each conductor ($C_1^{(A)}$ and $C_1^{(B)}$, $C_2^{(A)}$ and $C_2^{(B)}$, etc.) are spaced from each other. The conductors are mounted on the magnetic circuit 14, which may be of the slots-and-teeth kind. This is illustrated in the figure in a self-explanatory manner. The treatment zone TZ is located in the vicinity of the central region of the inductor 500b. The waves of the CVMF produced by the inductor parts located at two sides of the center region move towards each other (i.e., towards the treatment zone) with the same velocity $V_{CVMF}$.

It should be noted that the device 500b can also be used for in vitro treatment, for example, the treatment of seeds. Additionally, the device may comprise a pair of inductors 512 accommodated in a spaced-apart parallel relationship defining a gap therebetween.

Figure 10:
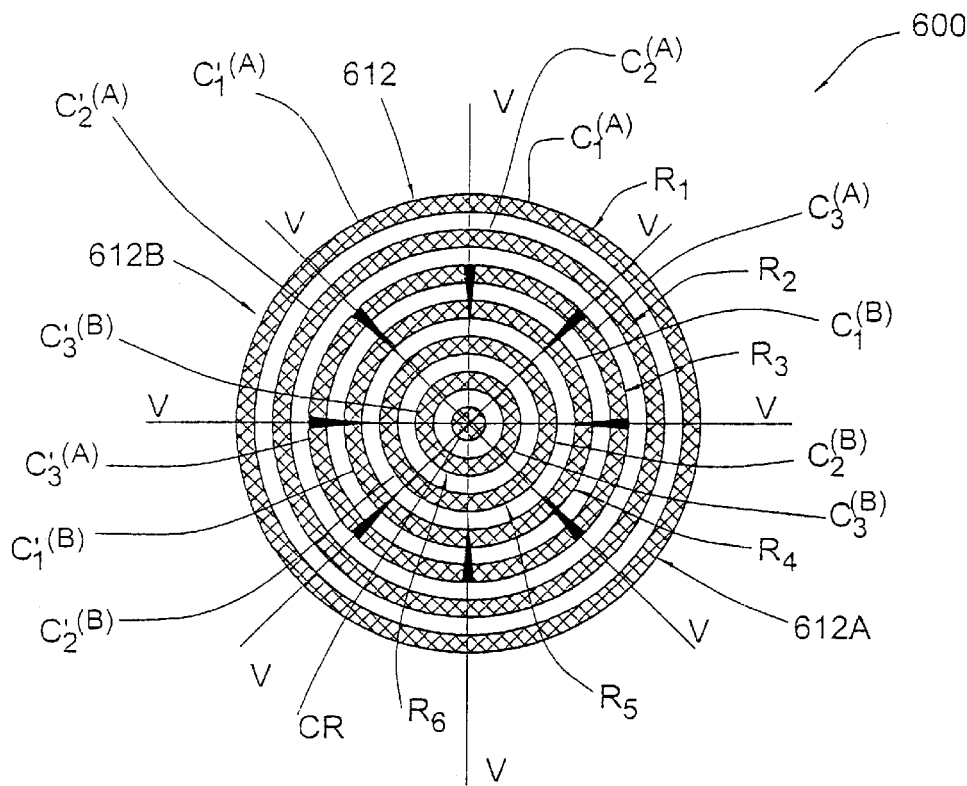
FIG. 10 illustrates another example of the implementation of a device according to the invention suitable for in vivo treatment of a biological material.

FIG. 10 exemplifies a device 600 suitable for in vivo treatment of a biological material, for example, by targeting pharmaceutical substances towards the biological material to be treated. In this example, an inductor 612 comprises ring-like conductive elements $R_1$–$R_6$ (concentric rings in the present example), arranged such that one semi-ring of each element is the conductor of one inductor part 612a, and the other semi-ring of each element is the conductor of the other inductor part 612b. More specifically, ring $R_1$ is formed by conductor parts $C_1^{(A)}$ and $C'_1^{(A)}$, ring $R_2$ is formed by conductor parts $C_2^{(A)}$ and $C'_2^{(A)}$, ring $R_3$ is formed by conductor parts $C_3^{(A)}$ and $C'_3^{(A)}$, ring $R_4$ is formed by conductor parts $C_1^{(B)}$ and $C'_1^{(B)}$, ring $R_5$ is formed by conductor parts $C_2^{(B)}$ and $C'_2^{(B)}$, and ring $R_6$ is formed by conductor parts $C_3^{(B)}$ and $C'_3^{(B)}$ etc. The treatment zone extends from a periphery region of the inductor 612 towards its center region CR. The electrical connection of the conductors is similar to that of the example of FIG. 9B. Thus, the waves of magnetic induction of the CVMF produced by the inductor 612 propagate radially towards the center region CR.

It should be noted, although not specifically shown, that by appropriately supplying the inductor, the direction of wave can be changed to the opposite one, namely the waves can be directed radially from the center region CR towards a periphery region of the inductor.

It should also be noted that such a ring-based inductor 612 can be used for in vitro treatment, for example, for hystological analysis. The device 600 may comprise two spaced-apart inductors 612, in which case the treatment zone would be located within a gap between the two inductors.

Figure 11:
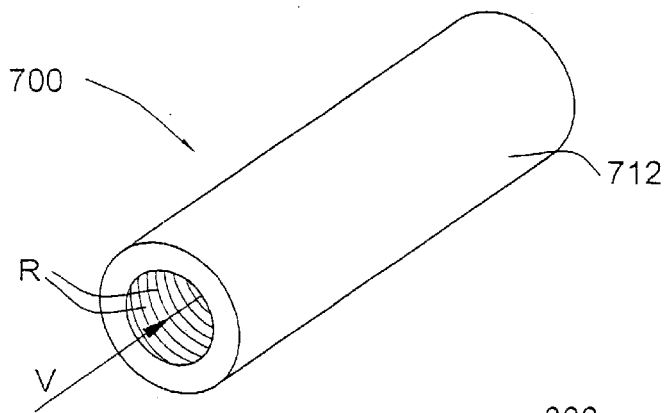
FIG. 11 illustrates yet another example of the implementation of a device according to the invention, which is suitable for in vivo treatment of a biological material, as well as for use with a bio-reactor.
Figure 12:
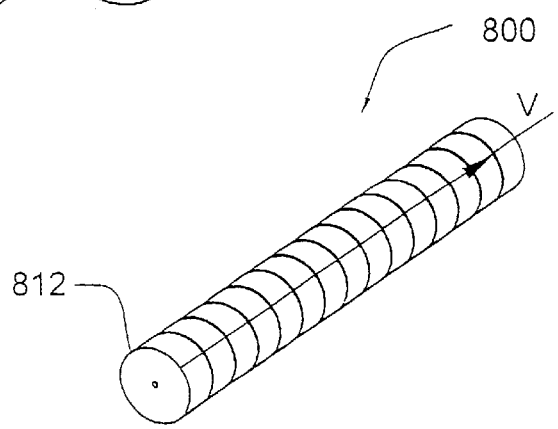
FIGS. 12 and 13 illustrate two different implementations, respectively, of a device according to the invention, suitable for use with a bio-reactor.
Figure 13:
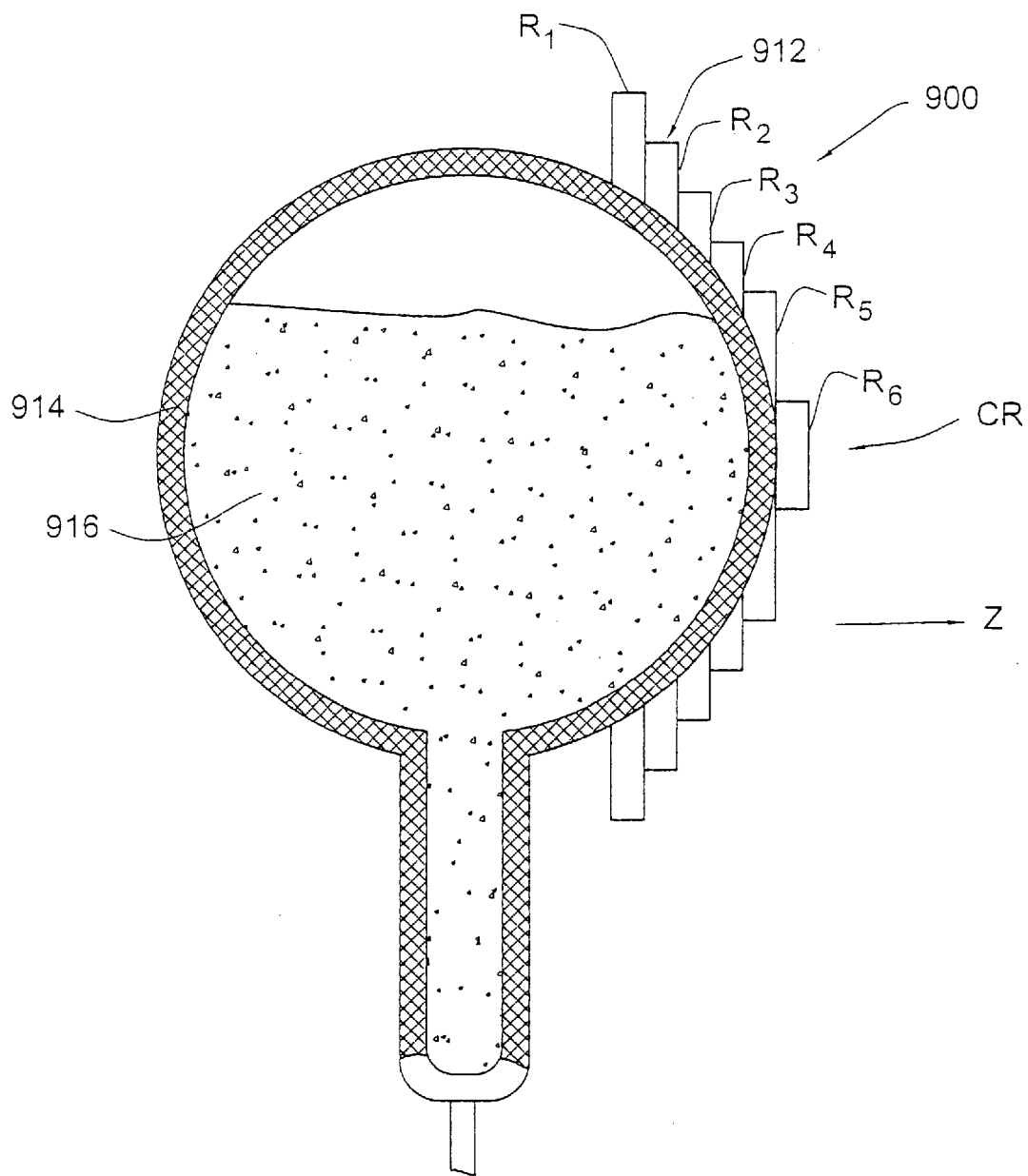

Reference is made to FIGS. 11, 12 and 13 showing different examples of a device according to the invention suitable for use with a bio-reactor.

In the example of FIG. 11, a device 700 comprises a hollow cylindrically shaped inductor 712 coupled to a power source, which is not specifically shown. The inductor 712 comprises a plurality of spaced-apart ring-like conductive elements R, the semi-rings of these conductive elements forming two inductor parts, as described above. The conductors can be accommodated and electrically connected to each other as in the example of either of FIGS. 9A and 9B. The treatment zone may be that located inside the cylinder and/or that located around the cylinder. Such a device in the form of a hollow cylinder can be used to treat or alleviate impotence problems.

In the example of FIG. 12, a device 800 comprises a rod-like inductor 812 constructed generally similar to the inductor 712, i.e., similar to the example of either of FIGS. 9A and 9B. The treatment zone is in the vicinity of the inductor 812 either extending along its axis or being located around the central region of the inductor 812.

According to the example of FIG. 13, a device 900 comprises an inductor 912 designed so as to cover the circumferential region of a spherical or cylindrical bio-reactor 914 containing a plant tissue culture 916. The inductor is designed generally similar to that of FIG. 10, namely, comprising a plurality of ring-like conductive elements $R_1$–$R_6$. Here, however, the inductor 912 is shaped like a concave lens, the rings $R_1$–$R_6$ being aligned along the Z-axis. The treatment zone TZ extends from a periphery region of the inductor 912 towards its central region CR of the inductor 912. The waves of the CVMF move towards and/or away the central region CR of the inductor.

EXAMPLE I

Manipulation of Plant Cuttings to Improve Rooting

Experimental Procedure 71582 cuttings of 13 different species of hard-to-root juniper plants were used. In the experiment 51938 were treated by the magnetic field and 19,644 served as control.

The plants were subjected to a CVMF utilizing the device as shown in FIG. 5.

The slot-like gap of the device had a width (working gap Δ) of 12 mm, a length of 200 mm, and a depth of 50 mm. The amplitude values of the magnetic induction were in the range 6–28 mT and the half-wavelength λ/2 of the wave of the magnetic induction was 23.4 mm.

The magnetic field source was connected to a commercial three phase power source of 50 Hz to provide said magnetic field.

During each treatment, several tens of cuttings were treated with the CVMF simultaneously for a period varying between 30–180 secs, and were then treated by the conventional means as described above.

It should be noted, that the slot-like space contained ambient air, water, or a medium solution. Where medium solution was used, it contained a growth hormone IBA having a concentration of 1,000–2,000 ppm.

The rooting process was followed for 4 months.

Results

Of cutting treated as described above, 45.8% sprouted roots.

Of a control plants, grown under the same conditions which did not receive the above treatment, 32.3% sprouted root.

As can be seen, treatment with the CVMF increased the rooting success of plant cuttings in treated plants as compared to non-treated control and about 41.8% (P=0.05 in Studet test).

EXAMPLE II

Propagation of Plant Microcultures

Typically, plant microcultures are propagated by placing plant tissue culture in an agar-filled growth vessel, the agar providing the culture with nutrients for a period of several weeks. The vessel is placed inside an incubator having a desired temperature and light emission, for several weeks until growth, of root, leaves, stem or all.

Experimental Procedure

The plant tissue cultures were placed in agar-filled growth vessels as previously known.

The growth vessels were then placed on a moving conveyor, so that each vessel sequentially passed successive regions of the manipulation zone defined by the magnetic field region, and was located within the manipulation zone during a preset time period defined by the velocity of the conveyor movement.

CVMF was produced by a device as shown in FIG. 7.

The half-wavelength $\lambda/2$ of the CVMF was larger than the depth (thickness, $\Delta$) of the agar layer.

The velocity of the movement of the vessels on the conveyor is in ten orders of magnitudes smaller than the velocity of movement of the wave of magnetic induction of the CVMF. As indicated above, the velocity of movement of the conveyor defines the treatment time.

In the specific example, the inductor, as shown in FIG. 7, had the length of 150 mm, width of 250 mm and the inductor was mounted below the conveyor belt. The velocity of the movement of the conveyor belt was adjusted so that each section of the tissue culture was subjected to the CVMF for a time period of 30–600 secs.

The depth of the agar-layer (working gap) $\Delta$ was not more than 15 mm (so that it was smaller than $\lambda/2$ which was 72 mm).

The amplitude values of the magnetic induction TZ volume was 11–42 mT.

Two tissue cultures were used: one of a bananas used to determine the leaf sprouting, and the other of potatoes used to determine the level of root sprouting. Both plant tissues were placed in a growth vessel of glass test tubes having a calibration of 25 mm and a height of 100 mm.

Treatment parameters were as follows:

For banana tissue culture—CVMF treatment time in Group A (comprising 38 plant tissue culture units) was 120 secs and in Group B (comprising 36 plant tissue culture units) was 240 secs, and control group was 35 untreated plant tissue culture units.

The growth was followed for 27 days.

For potatoes plant tissue culture—CVMF treatment in Group A (comprising 22 plant tissue units) was 120 sec and in Group B (23 plant tissue culture units) was 240 sec, and control group was 23 plant tissue culture units.

The growth was followed for 38 days.

Results

Banana plant tissue culture:

The improvement over control was of 25%, as indicated by additional number of leaves (Group A) and 17% (Group B), respectively (P=0.05 in Student test).

Potatoes plant tissue culture:

The improvement over control was of 53% (Group A) and 33% (Group B), respectively, was measured by additional number of roots (P=0.05 in Student test).

These results clearly indicate that subjection of tissue culture of plants to a coordinate-varying magnetic field significantly increases the propagation of plants (being either leaves or roots) from plant tissue culture.

An additional important feature was the fact that the amount of agar used by the treated banana plant tissue was 21% and 31%, for Group A and B respectively, (P=0.05 in Student test) smaller than the amount of agar used by the control and untreated plants. This indicates that the improved propagation of plants from plant tissue, was achieved together with a small utilization of nutrients by the plant, probably since the magnetic field improved diffusion and metabolism.

EXAMPLE III

Sprouting of Seeds

Experimental Procedure

Several layers of seeds were placed in a treatment vessel, having a height of about 20 mm (i.e., working gap $\Delta$).

The seeds were subjected to a coordinate-varying magnetic field provided by a two-part inductor as shown in FIG. 6.

The size of the gap between the two inductors should be smaller than $\lambda/2$ which was 72 mm ($\lambda/2>\Delta/2$).

The dimensions of each inductor were: length 150 mm, width 200 mm and gap 27 mm.

Seeds were placed inside the gap for a time period of 30–600 secs, and the magnetic field source was turn on and off, so that the ratio of the on:off time was 1:2.

The amplitude values of the magnetic induction per the surface area of the inductor was 17–38 mT, and the magnitude of the magnetic field per the depth of the seed layer was 18–22 mT).

500 melon seeds were subjected to this treatment, the seeds were planted, and the crop was harvested and its weight assessed.

Results

The melon crop weight of melons obtained from the treated seeds was 14% (P=0.05 Student test) higher than that of the melon crop weight obtained from untreated seeds. This indicates that the percentage of sprouting from treated seeds was significantly higher than the sprouting from untreated seeds.

Those skilled in the art will readily appreciate that various modifications and changes can be applied to the embodiments of the invention as hereinbefore exemplified without departing from its scope defined in and by the appended claims.

What is claimed is:

1. A device for the manipulation of a biological material by a magnetic field, comprising a magnetic field source coupled to a current source for producing said magnetic field, the device being characterized in that:

the current source is of a kind supplying an electric current of at least two electrical degree shifted phases;

the magnetic field source comprises a two-part inductor, each inductor part producing a coordinate varying magnetic field (CVMF), wherein each inductor part is formed by at least two conductors aligned in a spaced-apart relationship, each of the at least two conductors being connectable to a different phase of the current source, each of the at least two conductors having two spaced-apart parts arranged such that when the conductor is connected to the current source, the electric current will flow in its two parts in opposite directions, respectively, the conductor being arranged such that each two locally adjacent conductor parts are associated with two different phases of the electric current source;

a distance between the two conductor parts coupled to the same phase of the current source defines a half-wavelength $\lambda/2$ of a wave of magnetic induction of said CVMF, and is selected in accordance with a predetermined relation between the wavelength $\lambda$ and an effective space $\Delta$ within the magnetic field region defined by the dimensions of the biological material and its distance from the magnetic field source.

2. The device according to claim 1, wherein the two conductor parts of each conductor of one inductor part are electrically connected to each other through the corresponding conductor of the other inductor part.

3. The device according to claim 1, wherein said predetermined relation is such that λ/2>Δ, the biological material is to be manipulated when located at outer surface of either inductor part.

4. The device according to claim 1, wherein the two inductor parts are located in two spaced-apart parallel planes defining a gap between the two inductor parts.

5. The device according to claim 1, wherein the two inductor parts are located in the same plane.

6. The device according to claim 4, wherein the magnetic field region is located within the gap between the two inductor parts.

7. The device according to claim 6, wherein an additional magnetic field region is located in the vicinity of an outer surface of either inductor part.

8. The device according to claim 1, wherein the CVMF is of an uni-polar kind, the distance between each two locally adjacent amplitude values of the magnetic induction being the distance between two locally adjacent identical magnetic poles created by the inductor part.

9. The device according to claim 1, wherein the CVMF is of a bi-polar kind, the distance between each two locally adjacent amplitude values of the magnetic induction being the distance between two locally adjacent opposite magnetic poles created by the inductor part.

10. The device according to claim 1, wherein the magnetic field source is in the form of spaced-apart ring-like conductive elements, one semi-ring of each element being the conductor of the one inductor part, and the other semi-ring of each element being the conductor of the other inductor part.

11. A method for the manipulation of a biological material to change at least one physiological property of the biological material to obtain a desired effect, the method comprising the steps of creating a magnetic field defining a magnetic field region for the biological material to be located therein, the method being characterized in:

a) creating said magnetic field by creating a system of magnetic poles that changes its position in time along at least one coordinate and in at least one direction, said magnetic field being thereby a coordinate varying magnetic field (CVMF) that defines said magnetic field region and has an amplitude value of a wave of its magnetic induction continuously displaced along the magnetic field region in said at least one direction along said at least one coordinate, the magnitude of the magnetic induction being sufficient to cause said change of the at least one physiological property of the biological material;

b) selecting the wavelength λ of the wave of the magnetic induction and an effective space Δ within the magnetic field region, defined by the dimensions of the biological material and its location relative to the magnetic field source, in accordance with a predetermined condition of a relation between them; and c) locating the biological material within the magnetic field region for a time period sufficient for causing said change to obtain said desired effect.

12. The method according to claim 11, wherein said biological material is from a plant source.

13. The method according to claim 12, wherein the biological material is selected from the group consisting of: plant cuttings, plant seeds and plant tissue culture.

14. The method according to claim 11, wherein the direction of movement of the system of poles is periodically changed to the opposite one.

15. The method according to claim 11, wherein the creation of the magnetic field is activated periodically.

16. A device for carrying out the method of claim 11 for the manipulation of a biological material by the magnetic field, comprising a magnetic field source coupled to a current source for producing said magnetic field, the device being characterized in that:

the current source is of a kind supplying an electric current of at least two electrical degree shifted phases;

the magnetic field source comprises a two part inductor, each inductor part producing a coordinate varying magnetic field (CVMF), wherein each inductor part is formed by at least two conductors aligned in a spaced-apart relationship, each of the at least two conductors being connectable to a different phase of the current source, each of the at least two conductors having two spaced-apart parts arranged such that when the conductor is connected to the current source, the electric current will flow in its two parts in opposite directions, respectively, the conductors being arranged such that each two locally adjacent conductor parts are associated with two different phases of the electric current source;

a distance between the two conductor parts coupled to the same phase of the current source defines a half-wavelength λ/2 of a wave of magnetic induction of said CVMF, and is selected in accordance with a predetermined relation between the wavelength λ and an effective space Δ within the magnetic field region defined by the dimensions of the biological material and its distance from the magnetic field source.

* * * * *